(12) United States Patent
Dewdney et al.

(10) Patent No.: US 7,189,731 B2
(45) Date of Patent: Mar. 13, 2007

(54) SUBSTITUTED 7-AZAQUINAZOLINE COMPOUNDS USEFUL AS P38 KINASE INHIBITORS

(75) Inventors: Nolan James Dewdney, San Jose, CA (US); David Michael Goldstein, San Jose, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 448 days.

(21) Appl. No.: 10/824,980

(22) Filed: Apr. 15, 2004

(65) Prior Publication Data

US 2004/0209903 A1 Oct. 21, 2004

Related U.S. Application Data

(60) Provisional application No. 60/463,229, filed on Apr. 16, 2003.

(51) Int. Cl.
*A01N 43/90* (2006.01)
*A61K 31/519* (2006.01)
*C07D 471/00* (2006.01)

(52) U.S. Cl. .................. 514/264.11; 544/279
(58) Field of Classification Search ........... 514/264.11; 544/279
See application file for complete search history.

(56) References Cited

U.S. PATENT DOCUMENTS

| | | | |
|---|---|---|---|
| 3,594,480 A | 7/1971 | Cronin et al. | |
| 4,672,116 A | 6/1987 | Bandurco et al. | |
| 5,084,463 A | 1/1992 | Butera et al. | |
| 6,313,294 B1 | 11/2001 | Chou et al. | |
| 2002/0061879 A1 | 5/2002 | Garvey et al. | |

FOREIGN PATENT DOCUMENTS

| | | |
|---|---|---|
| EP | 1 110 552 A1 | 6/2001 |
| WO | WO 92/01675 A1 | 2/1992 |
| WO | WO 98/38984 A2 | 9/1998 |
| WO | WO 01/32632 A2 | 5/2001 |
| WO | WO 01/38315 A1 | 5/2001 |
| WO | WO 01/64646 A2 | 9/2001 |
| WO | WO 02/08224 A1 | 1/2002 |
| WO | WO 02/085908 A1 * | 4/2002 |
| WO | WO 02/50045 A1 | 6/2002 |
| WO | WO 02/085908 A1 | 10/2002 |
| WO | WO/2002/090360 * | 11/2002 |

OTHER PUBLICATIONS

Bodor, et al., "Chemical Approaches to Drug Delivery," Encyclopedia of Controlled Drug Delivery, 1999, John Wilery & Sons, 285-298.*

Hashimoto, et al., "Seledtive Inhibitor of p38 Mitogen-Activated Protein Kinase Inhibits Lipopolysaccharide-Induced Interleukin-8 Expression in Human Pulmonary Vascular Endothelial Cells," J. of Pharm & Exp. Therap., vol. 293, No. 2, pp. 370-375, 2000.*

Hensley, et al., "p38 Kinase is Activated in the Alzheimer's Disease Brain," J. of Neurochem., vol. No. 5, 1999, pp. 2053-2058.*

Johnson, et al., "Mitogen-Activated Protein Kinase Pathways Mediated by ERK, JNK and p38 Protein Kinases," Science, vol. 298, Dec. 6, 2002, 1911-1912.*

Blease, "Targeting Kinases in Asthma," Expert Opin. Investig. Drugs, 2005, vol. 14, No. 10, 1213-1220.*

Lee, et al., "p38 Mitogen-Activated Protein Kinase Inhibitors—Mechanisms and Therapeutic Potentials," Pharmacol. Ther., May-Jun. 1999;82(2-3):389-97.*

Lee, J.C., et al., "p38 Mitogen-Activated Protein Kinase Inhibitors Mechanisms and Therapeutic Potentials," *Pharmacol. Ther.* 82 (1999) 389-397.

Newton, R., et al., "New aspects of p38 mitogen activated kinase (MAPK) biology in lung inflammation," *Drug Discovery Today* 3 (2006) 53-61.

* cited by examiner

*Primary Examiner*—Deepak Rao
*Assistant Examiner*—Cecilia Jaisle
(74) *Attorney, Agent, or Firm*—Grant D. Green

(57) ABSTRACT

Compounds having the formula (I) or (II),

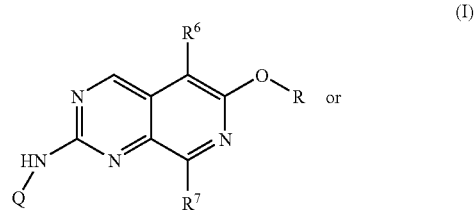

(I)

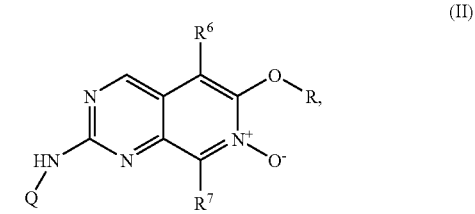

(II)

are useful as p38 kinase inhibitors, wherein R is an optionally substituted alkyl, cycloalkyl, or aryl; $R^6$ is hydrogen or lower alkyl; $R^7$ is hydrogen or a non-interfering substituent, and Q is a non-aromatic moiety as defined in the specification.

19 Claims, No Drawings

SUBSTITUTED 7-AZAQUINAZOLINE COMPOUNDS USEFUL AS P38 KINASE INHIBITORS

RELATED APPLICATIONS

This applications claims priority from U.S. provisional patent application Ser. No. 60/463,229, filed Apr. 16, 2003, incorporated herein by reference in full.

FIELD OF THE INVENTION

The present invention relates to certain quinazoline compounds useful as p38 protein kinase inhibitors. In particular, the present invention relates to 2-amino-6-phenyloxy substituted 7-azaquinazoline compounds, pharmaceutical preparations comprising the same, and methods for using them.

BACKGROUND OF THE INVENTION

Mitogen-activated protein kinases (MAP) are a family of proline-directed serine/threonine kinases that activate their substrates by dual phosphorylation. The kinases are activated by a variety of signals including nutritional and osmotic stress, UV light, growth factors, endotoxin, and inflammatory cytokines. One group of MAP kinases is the p38 kinase group which includes various isoforms (e.g., p38α, p39β, p38γ and p38δ). The p38 kinases are responsible for phosphorylating and activating transcription factors (as well as other kinases), and are themselves activated by physical and chemical stress, pro-inflammatory cytokines, and bacterial lipopolysaccharide.

More importantly, the products of the p38 phosphorylation have been shown to mediate the production of inflammatory cytokines, including TNF, IL-1, IL-6, and cyclooxygenase-2 (COX-2). Each of these cytokines has been implicated in numerous disease states and conditions. For example, TNF-α is a cytokine produced primarily by activated monocytes and macrophages. Excessive or unregulated production of TNF-α has been implicated as playing a causative role in the pathogenesis of rheumatoid arthritis. More recently, inhibition of TNF production has been shown to have broad application in the treatment of inflammatory conditions, inflammatory bowel disease, Alzheimer's disease, Crohn's disease, multiple sclerosis, and asthma.

Additionally, TNF has been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpes virus-7 (HHV-7), human herpes virus-8 (HHV-8), pseudorabies, and rhinotracheitis, among others.

Similarly, IL-1 is produced by activated monocytes and macrophages and plays a role in many pathophysiological responses including rheumatoid arthritis, fever and reduction of bone resorption.

The inhibition of these cytokines by inhibition of the p38 kinase would be beneficial in controlling, reducing and alleviating many of these disease states. p38 MAP kinase inhibitors have demonstrated efficacy in several disease models including arthritis and other joint diseases, sepsis, stroke, myocardial injury, respiratory inflammatory diseases such as chronic obstructive pulmonary disease and asthma, and a wide range of inflammatory conditions. The present invention provides certain 2-amino-6-phenoxy substituted quinazoline compounds useful in inhibiting p38 kinase. U.S. patent application Ser. No. 10/824,731, filed concomitantly herewith and assigned to the present assignee, discloses 2-amino-6-phenoxy substituted quinazoline compounds useful as p38 kinase inhibitors, and the entire contents of said application is hereby incorporated herein by reference.

SUMMARY OF THE INVENTION

The present invention is directed to compounds having the Formula (I) or (II):

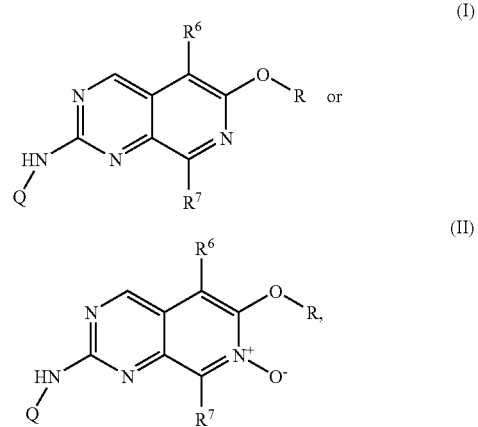

and isomers, prodrugs, and pharmaceutically-acceptable salts thereof, wherein: R is selected from:
(a) alkyl optionally-substituted with one to three of $R^{17}$;
(b) cycloalkyl optionally substituted with one, two or three groups selected from $R^{18}$; and
(c) optionally-substituted aryl;

Q is selected from alkyl, cycloalkyl, substituted cycloalkyl, heterocyclyl, substituted heterocyclyl, and alkyl substituted with one, two or three of halogen, cyano, —$OR^8$, —$SR^8$, —$C(=O)R^8$, —$C(O)_2R^8$, —$C(=O)NR^8R^9$, —$C(O)_2NR^8R^9$, —$S(O)_pR^{10}$, —$S(O)_2NR^8R^9$, —$NR^8R^9$, cycloalkyl, substituted cycloalkyl, heterocyclyl, and/or substituted heterocyclyl;

$R^6$ is hydrogen or lower alkyl;

$R^7$ is selected from hydrogen, alkyl, substituted alkyl, halogen, cyano, nitro, hydroxy, alkoxy, haloalkoxy, amino, alkylamino, and optionally-substituted cycloalkyl, heterocyclyl, aryl, or heteroaryl;

$R^8$ and $R^9$ are (i) independently selected from hydrogen, alkyl, haloalkyl, hydroxyalkyl, alkoxyalkyl, cycloalkyl, substituted cycloalkyl, heterocyclyl, and substituted heterocyclyl; or (ii) when $R^8$ and $R^9$ are attached to the same nitrogen atom (as in —$C(=O)NR^8R^9$, —$S(O)_2NR^8R^9$, and —$NR^8R^9$), $R^8$ and $R^9$ may be taken together to form an optionally-substituted heterocyclyl ring;

$R^{10}$ is alkyl, hydroxyalkyl, alkoxyalkyl, cycloalkyl, substituted cycloalkyl, heterocyclyl, or substituted heterocyclyl;

$R^{17}$ is at each occurrence independently selected from halogen, haloalkoxy, haloalkyl, alkoxy, or optionally-substituted phenyl, benzyl, phenyloxy, benzyloxy, or cycloalkyl;

$R^{18}$ is at each occurrence independently selected from alkyl, substituted alkyl, halogen, haloalkyl, haloalkoxy, cyano, alkoxy, acyl, alkoxycarbonyl, alkylsulfonyl, or optionally-substituted phenyl, phenyloxy, benzyloxy, cycloalkyl, heterocyclyl, or heteroaryl; and p is 1 or 2.

Also provided are pharmaceutical compositions containing at least one compound according to Formula (I) and/or (II), or a pharmaceutically-acceptable salt thereof.

DETAILED DESCRIPTION OF THE INVENTION

Definitions

The following definitions shall apply in the instant specification and claims, unless otherwise specifically indicated.

As used herein, the term "alkyl" means a linear or branched, saturated monovalent hydrocarbon moiety of one to eight carbon atoms (preferably one to six carbon atoms), e.g., methyl, ethyl, n-propyl, 2-propyl, tert-butyl, pentyl, and the like. "Lower alkyl" means an alkyl of one to four carbon atoms. When a subscript is used herein following a carbon atom, the subscript refers to the number of carbon atoms the named group may contain. Thus, for example, $C_{1-4}$alkyl means an alkyl of one to four carbon atoms (i.e., lower alkyl) including methyl, ethyl, propyl, iso-propyl, butyl, and tert-butyl.

"Alkylene" means a linear or branched, saturated divalent hydrocarbon moiety of one to eight (preferably one to six) carbon atoms, e.g., methylene, ethylene, propylene, and the like. When reference is made to an alkylene linker group, as in —Y—S(O)$_2$R, —Y—C(O)$_2$NRR, —Y—S(O)$_2$NRR, and so forth, wherein Y is alkylene, it should be understood that the alkylene may be a straight or branched-chain alkylene, and the referenced substituent may be attached to any carbon atom of the alkylene straight or branched chain. Thus, for example, the group —Y—S(O)$_2$R, may include, without limitation, —CH$_2$—S(O)$_2$R, —CH$_2$—CH[S(O)$_2$R]—CH$_3$, —CH$_2$—CH{CH$_2$CH[S(O)$_2$R]CH$_3$}CH$_3$, and so forth.

When the term "alkyl" is used as a suffix following another term, as in "phenylalkyl," or "hydroxyalkyl," this is intended to refer to an alkyl group, as defined above, being substituted with one or more (preferably one) substituent selected from the other, specifically-named group. Thus, "phenylalkyl" includes benzyl, phenylethyl, 2-phenylbutyl, and so forth. "Hydroxyalkyl" includes 2-hydroxyethyl, 1-(hydroxymethyl)-2-methylpropyl, 3,4-dihydroxybutyl, and so forth. Accordingly, as used herein, the term "hydroxyalkyl" is used to define a subset of heteroalkyl groups defined below. In the case of a "substituted cycloalkylalkyl," this is intended to refer to an alkyl group, as defined above, being substituted with one to two substituted cycloalkyl groups, as defined below, and likewise, a "substituted heterocycloalkylalkyl" refers to an alkyl group, as defined above, being substituted with one to two substituted heterocyclyl groups, as defined below.

The term "substituted alkyl" refers to an alkyl group as defined above having one, two, three, or four substituents (preferably one to two), independently selected from the group consisting of halo, haloalkoxy, trifluoromethyl, cyano, nitro, —OR$^a$, —SR$^a$, —S(O)R$^c$, —S(O)$_2$R$^c$, —C(=O)R$^a$, —C(=O)NR$^a$R$^b$, —C(O)$_2$R$^a$, —C(O)$_2$NR$^a$R$^b$, —S(O)$_2$NR$^a$R$^b$, —NR$^a$R$^b$, aryl, substituted aryl, heteroaryl, substituted heteroaryl, cycloalkyl, substituted cycloalkyl, heterocyclyl, and/or substituted heterocyclyl, wherein R$^a$ and R$^b$ are independently selected from hydrogen, $C_{1-6}$alkyl, aryl, heteroaryl, cycloalkyl, and heterocyclyl, and R$^c$ is selected from $C_{1-6}$alkyl, aryl, heteroaryl, cycloalkyl, and heterocyclyl, and each of R$^a$, R$^b$, and R$^c$ in turn is optionally substituted with one, two, or three of alkyl, halo, haloalkyl, hydroxy, alkoxy, haloalkoxy, cyano, amino, alkylamino, —SO$_2$(alkyl), CO$_2$H, CO$_2$(alkyl), C(=O)H, and/or C(=O)alkyl, and/or a $C_{1-4}$ alkyl substituted with one to two of halo, hydroxy, alkoxy, haloalkoxy, cyano, amino, alkylamino, —SO$_2$(alkyl), CO$_2$H, CO$_2$(alkyl), C(=O)H, and/or C(=O)alkyl.

"Acyl" refers to the group —C(=O)R', wherein R' is alkyl, substituted alkyl, aryl, or arylalkyl.

"Alkoxy" refers to the group OR', wherein R' is alkyl or substituted alkyl. A "lower alkoxy" is a group —OR' wherein R' is $C_{1-4}$alkyl.

"Alkoxycarbonyl" refers to the group COOR', wherein R' is alkyl or substituted alkyl as defined above.

"Alkylsulfonyl" refers to the group —S(O)$_2$R', wherein R' is alkyl or substituted alkyl as defined above.

When reference is made herein to a carboxmide group —CO$_2$NRR (e.g., as in —C(O)$_2$NR$^8$R$^9$), it should be understood this is intended to refer to the group —O—C(=O)—NRR.

When the term "oxy" is used as a suffix following another specifically-named group, as in "aryloxy", "heteroaryloxy," or "arylalkyloxy", this means that an oxygen atom is present as a linker to the other, specifically-named group. Thus, for example, "aryloxy" refers to the group —O—R, wherein R is aryl; "heteroaryloxy" refers to the group —O—R', wherein R' is heteroaryl; and "arylalkyloxy" refers to the group —O—R", wherein R" is arylalkyl such as benzyl. Similarly, a "substituted aryloxy" means the group —O—R, wherein R is substituted aryl, and a "substituted heteroaryloxy" means the group —O—R', wherein R' is substituted heteroaryl.

"Amino" refers to the group NH$_2$. Thus, an aminoalkyl refers to an alkyl group having an amino substituent, e.g., —CH$_2$—NH$_2$, —CH$_2$—CH$_2$—NH$_2$, —CH$_2$—CH(NH$_2$)—CH$_3$, and so forth. An alkylamino refers to monoalkylamino groups having the formula —NHR, as well as dialkylamino groups having the formula —NRR, wherein each R is independently alkyl, substituted alkyl, heterocyclyl, substituted heterocyclyl, cycloalkyl, or substituted cycloalkyl. Accordingly, an alkylaminoalkyl refers to an alkyl group substituted by one to two of —NHR and/or —NRR. A "lower aminoalkyl" refers to a group —NHR' or —NR'R', wherein each R' is $C_{1-4}$alkyl.

The term "aryl" refers to a monovalent, monocyclic or bicyclic moiety in which at least one of the rings is an aromatic, carbocyclic moiety. Thus, the term "aryl" includes phenyl, 1-napthyl, and 2-napthyl. The term "aryl" also includes phenyl rings having fused thereto a second non-aromatic carbocyclic ring, or a heteroaryl or heterocyclic ring such as benzothienyl, benzopyrazolyl, benzopiperadinyl, benzocyclohexyl, and the like, with the understanding, however, that the point of attachment will be to the phenyl ring.

A "substituted aryl" is an aryl group as defined above having one or more (preferably one, two, or three) substituents independently selected from the group consisting of halo, haloalkyl, haloalkoxy, cyano, nitro, —Y—R$^p$, —Y-aryl, —Y-heteroaryl, —Y-cycloalkyl, —Y-heterocyclyl, —Y—OR$^p$, —Y—NR$^p$R$^q$, —Y—C(=O)R$^p$, —Y—C(O)$_2$R$^p$, —Y—C(=O)NR$^p$R$^q$, —Y—C(O)$_2$NR$^p$R$^q$, —Y—S(O)$_{0-2}$R$^p$, —Y—NRS(O)$_2$R$^q$, —Y—S(O)$_2$NR$^p$R$^q$, and/or —Y—NRC(=O)NR$^p$R$^q$, where Y is absent or a $C_{1-4}$alkylene group, R is hydrogen, lower alkyl, or hydroxy$C_{1-4}$alkyl, and R$^p$ and R$^q$ are independently selected from hydrogen, alkyl, aryl, heteroaryl, cycloalkyl, and heterocyclyl, except when said substituent is —YS(O)$_{1-2}$R$^p$ or —Y—NRS(O)$_2$R$^p$, then R$^p$ in these instances is not hydrogen. In each instance, each of R$^p$ and/or R$^q$ in turn is optionally substituted with one to two of alkyl, halo, cyano, hydroxy, alkoxy, amino, alkylamino, haloalkyl, haloalkoxy, hydroxyalkyl, alkoxyalkyl, aminoalkyl, alkylaminoalkyl, —SO$_2$(alkyl), CO$_2$H, CO$_2$(alkyl), C(=O)H, and/or C(=O) alkyl. A preferred group of aryl substituents are those selected from alkyl, haloalkyl, halo, hydroxy, amino, alkylamino, haloalkoxy and alkoxy. Within this group, especially preferred aryl substituents are halo, alkyl, and alkoxy. More specifically, the term "substituted aryl" includes, but is not limited to, fluorophenyl, difluorophenyl, chlorophenyl, methoxyphenyl, and the like.

The term "carbocyclic" means a cyclic moiety in which all ring atoms are carbon atoms, including saturated, partially unsaturated, and unsaturated rings.

The term "cycloalkyl" as used herein refers to saturated or partially unsaturated, monovalent, monocyclic carbocyclic moieties of three to seven ring carbon atoms and further includes such rings having a carbon-carbon bridge of one, two, or three bridgehead carbon atoms, and/or having a second ring fused thereto, with the understanding that said second fused ring may be a non-aromatic carbocyclic or heterocyclic ring in which case the point of attachment will be to the non-aromatic carbocyclic ring moiety. Thus, the term "cycloalkyl" includes such rings as cyclopropyl, cyclopentyl, cyclopentenyl, cyclohexyl, cyclohexenyl, and the like. Additionally, one or two carbon atoms of a cycloalkyl group may optionally contain a carbonyl oxygen group, e.g., one or two atoms in the ring may be a moiety of the formula —C(=O)—.

A "substituted cycloalkyl" is a cycloalkyl group as defined above having one, two, or three substituents independently selected from the group consisting of halo, haloalkyl, haloalkoxy, cyano, nitro, —Y—R$^s$, —Y-cycloalkyl, —Y-heterocyclyl, —Y—OR$^s$, —Y—NR$^s$R$^t$, —Y—C(=O)R$^s$, —Y—C(O)$_2$R$^s$, —Y—C(=O)NR$^s$R$^t$, —Y—C(O)$_2$NR$^s$R$^t$, —Y—S(O)$_{0-2}$R$^s$, —Y—NRS(O)$_2$R$^s$, —Y—S(O)$_2$NR$^s$R$^t$, and/or —Y—NRC(=O)NR$^s$R$^t$, wherein Y is absent or a C$_{1-4}$alkylene group, R is hydrogen, lower alkyl, or hydroxyC$_{1-4}$alkyl, and R$^s$ and R$^t$ are independently selected from hydrogen, alkyl, cycloalkyl, and heterocyclyl, except when said substituent is —YS(O)$_{1-2}$R$^s$ or —Y—NRS(O)$_2$R$^s$, then R$^s$ in these instances is not hydrogen. In each instance, each of R$^s$ and/or R$^t$ in turn is optionally substituted with one to two of lower alkyl, halo, cyano, hydroxy, alkoxy, amino, alkylamino, haloalkyl, haloalkoxy, hydroxyalkyl, alkoxyalkyl, aminoalkyl, alkylaminoalkyl, —SO$_2$(alkyl), CO$_2$H, CO$_2$(alkyl), C(=O)H, and/or C(=O)alkyl. Preferred substituents for substituted cycloalkyl groups include -(alkylene)$_n$-hydroxy, -(alkylene)$_n$-lower alkoxy, -(alkylene)$_n$—S(O)$_2$(lower alkyl), and -(alkylene)$_n$—CO$_2$(lower alkyl), where n is 0, 1, or 2.

The term "halo," "halide" or "halogen," when referring to a substituent means fluoro, chloro, bromo, or iodo (preferably fluoro or chloro).

The term "haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all alkyl hydrogen atoms are replaced by fluorine atoms.

The term "haloalkoxy" means a haloalkyl group as defined above linked through an oxygen atom, e.g., it includes —O—CH$_2$Cl, —O—CF$_3$, —O—CH$_2$CF$_3$, —O—CH$_2$CCl$_3$, and the like.

The term "heteroalkyl" as used herein means an alkyl moiety defined above, wherein one, two or three hydrogen atoms have been replaced with a substituent independently selected from the group consisting of —OR$^d$, —NR$^d$R$^e$, and S(O)$_n$R$^d$ (where n is an integer from 0 to 2), with the understanding that the point of attachment of the heteroalkyl moiety is through a carbon atom, wherein R$^d$ and R$^e$ are selected from hydrogen, alkyl, substituted alkyl (but not including arylalkyl or heteroarylalkyl), cycloalkyl, substituted cycloalkyl, heterocyclyl, and substituted heterocyclyl, except when R$^d$ is attached to S(O)$_n$R$^d$ and n is 1 or 2, then R$^d$ is not hydrogen. Additionally, when R$^d$ and R$^e$ are attached to the same nitrogen atom, they may be taken together to form an optionally-substituted heterocyclyl or heteroaryl ring. Representative examples include, but are not limited to, 2-hydroxyethyl, 3-hydroxypropyl, 2-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, methylaminosulfonylmethyl, methylaminosulfonylethyl, methylaminosulfonylpropyl, 2-hydroxyethyl, 3-hydroxypropyl, 2-hydroxymethylethyl, 2,3-dihydroxypropyl, and so forth.

"Heterocyclo," "heterocyclyl," or "heterocyclic" refers to a saturated or partially-unsaturated non-aromatic monocyclic or bicyclic moiety in which one or two ring atoms are heteroatoms selected from N, O, or S(O)$_n$ (where n is an integer from 0 to 2), the remaining ring atoms being carbon atoms, and additionally, one or two carbon atoms may optionally contain a carbonyl oxygen group, e.g., one or two atoms in the ring may be a moiety of the formula —C(=O)—. Thus, the term heterocyclyl includes rings such as tetrahydropyranyl, tetrahydrofuryl, piperidinyl, piperazinyl, morpholinyl, pyrrolidinyl, pyrrolinyl, imidazolidinyl, imidazolinyl, and the like. In the case of a bicyclic heterocyclyl, one of the two rings may be a non-aromatic carbocyclic ring with the point of attachment, however, being to the heterocyclic ring.

A "substituted heterocyclyl" or "substituted heterocycle" refers to a heterocyclyl group as defined above having one, two, or three substituents (preferably one to two substituents) selected from the group consisting of halo, haloalkyl, haloalkoxy, cyano, nitro, —Y—R$^s$, —Y-cycloalkyl, —Y-heterocyclyl, —Y—OR$^s$, —Y—NR$^s$R$^t$, —Y—C(=O)R$^s$, —Y—C(O)$_2$R$^s$, —Y—C(=O)NR$^s$R$^t$, —Y—C(O)$_2$NR$^s$R$^t$, —Y—S(O)$_{0-2}$R$^s$, —Y—NRS(O)$_2$R$^s$, —Y—S(O)$_2$NR$^s$R$^t$, and/or —Y—NRC(=O)NR$^s$R$^t$, wherein Y, R, R$^s$ and R$^t$ are as defined above for substituted cycloalkyl groups, such that R$^s$ and R$^t$ are, in turn, at each instance independently optionally substituted with one to two further groups as recited above in the definition for substituted cycloalkyl. Preferred substituents for substituted heterocyclyl groups include -(alkylene)$_n$-hydroxy, -(alkylene)$_n$-lower alkoxy, -(alkylene)$_n$—S(O)$_2$(lower alkyl), and -(alkylene)$_n$—CO$_2$(lower alkyl), where n is 0, 1, or 2.

"Heteroaryl" means a monovalent, monocyclic aromatic moiety of 5 to 6 ring atoms containing one, two, three, or four ring heteroatoms, each independently selected from N, O, or S, the remaining ring atoms being carbon, and it also includes such rings having a second ring fused thereto of five to six ring atoms, wherein the second fused ring may be aromatic or non-aromatic and may be carbocyclic, heterocyclic, or a heteroaryl ring, with the understanding, however, that in such cases the point of attachment will be to an aromatic ring containing at least one heteroatom. Thus, the term heteroaryl includes, but is not limited to, pyridyl, furyl, thiophenyl, thiazolyl, isothiazolyl, triazolyl, imidazolyl, isoxazolyl, pyrrolyl, pyrazolyl, pyrimidinyl, benzofuryl, isobenzofuryl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and derivatives thereof.

A "substituted heteroaryl" is a heteroaryl ring as defined above having one, two or three (preferably one or two) substituents selected from the group consisting of halo, haloalkyl, haloalkoxy, cyano, nitro, —Y—R$^p$, —Y-aryl, —Y-heteroaryl, —Y-cycloalkyl, —Y-heterocyclyl, —Y—OR$^p$, —Y—NR$^p$R$^q$, —Y—C(=O)R$^p$, —Y—C(O)$_2$R$^p$, —Y—C(=O)NR$^p$R$^q$, —Y—C(O)$_2$NR$^p$R$^q$, —Y—S(O)$_{0-2}$R$^p$, —Y—NRS(O)$_2$R$^q$, —Y—S(O)$_2$NR$^p$R$^q$, and/or —Y—NRC(=O)NR$^p$R$^q$, wherein Y, R, R$^p$ and R$^q$ are as defined above for substituted aryl groups, such that R$^p$ and R$^q$ are, in turn, at each instance independently optionally substituted with one to two further substituents as recited above in the definition for substituted aryl. Preferred substituents for substituted heteroaryl groups include alkyl, haloalkyl, heterocyclyl, halo, nitro, cyano, and -(alkylene)$_n$—CO$_2$R (where n is 0 or 1 and R is hydrogen or alkyl).

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optional" or "optionally" means that the subsequently described event may but need not occur, and it includes instances where the event occurs and instances in which it does not. For example, "optionally-substituted cycloalkyl" refers to both cycloalkyl groups and substituted cycloalkyl groups, as defined above. When the term "optionally-substituted" precedes a number of different types of rings in one line or string, e.g., as in "optionally-substituted cycloalkyl or heterocyclyl", or "optionally-substituted carbocyclic or heterocyclic ring," or "optionally-substituted aryl, heteroaryl, cycloalkyl, or heterocyclyl," it is intended that the term "optionally-substituted" modifies each of the rings identified in the line or string.

When the term "optionally-substituted" is used with respect to a particularly-named cyclic group, such as "optionally-substituted cyclohexyl," or "optionally-substituted piperidinyl," it should be understood that the optional substituents for such particularly-named rings may be selected from the group of substituents recited above with respect to which the genus of which the particularly-named group is a member. Thus, for example, an "optionally-substituted cyclohexyl" may be an unsubstituted cyclohexyl or a cyclohexyl group having one, two, or three substituents selected from those recited above for substituted cycloalkyl.

When reference is made herein to the C5, C6, 7-aza, or C8 carbon atoms of the quinazoline ring, the numbering of the ring atoms is intended to be as follows:

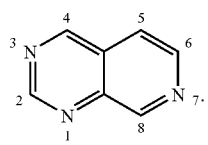

"Pharmaceutically acceptable excipient" means an excipient that is useful in preparing a pharmaceutical composition that is generally safe, non-toxic and neither biologically nor otherwise undesirable. The term includes excipients that are acceptable for veterinary use as well as human pharmaceutical use. A "pharmaceutically acceptable excipient" as used in the specification and claims includes both one and more than one such excipient.

"Pharmaceutically acceptable salt" of a compound means a salt that is generally safe, non-toxic and neither biologically nor otherwise undesirable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to an atom or group of atoms that is attached to a reactive group in a molecule and masks, reduces, or prevents the reactivity of the group to which it is attached. Examples of protecting groups can be found in Green and Wuts, *Protective Groups in Organic Chemistry* (Wiley, 2$^{nd}$ ed. 1991), and Harrison and Harrison et al., *Compendium of Synthetic Organic Methods*, Vols. 1–8 (John Wiley and Sons, 1971–1996). Representative amino protecting groups include formyl, acetyl, trifluoroacetyl, benzyl, benzyloxycarbonyl (CBZ), tertbutoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitroveratryloxycarbonyl (NVOC), and the like. Representative hydroxy protecting groups include those where the hydroxy group is either acylated or alkylated such as with benzyl or lower alkyl and trityl ethers as well as alkyl ethers, tetrahydropyranyl ethers, trialkylsilyl ethers, and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the progression of the disease, i.e., arresting or reducing the development of the disease or its symptoms; and (3) relieving the disease, i.e., causing regression of the disease or its symptoms.

"A therapeutically effective amount" means the amount of a compound that, when administered to a mammal for treating a disease, is sufficient to effect a treatment for the disease. The "therapeutically effective amount" will vary depending on such factors as the compound being administered, the type of disease being treated, the progression or severity of the disease state, and the age, weight, and general health of the mammal being treated.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the (R) and (S) sequencing rules of Cahn and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing different enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures (racemic or otherwise) thereof. The methods for the determination of stereochemistry and the separation of stereoisomers are well-known in the art (see March, *Advanced Organic Chemistry*, Chap. 4, 4th edition, John Wiley and Sons, New York [1992]).

PREFERRED EMBODIMENTS

While the definition of this invention is set forth in the Summary of the Invention, certain compounds of Formula (I) are preferred.

Preferred compounds according to the invention are those having Formula (Ip),

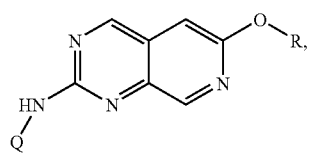

(Ip)

and isomers, prodrugs, and pharmaceutically-acceptable salts thereof, wherein:

R is optionally-substituted aryl;

Q is alkyl substituted with one, two or three of —OR$^8$, —SR$^8$, —C(=O)R$^8$, —C(O)$_2$R, —C(=O)NR$^8$R$^9$, —S(O)$_p$R$^{10}$, —C(O)$_2$NR$^8$R$^9$, —S(O)$_2$NR$^8$R$^9$, —NR$^8$R$^9$, cycloalkyl, substituted cycloalkyl, heterocyclyl, and/or substituted heterocyclyl;

R$^8$ and R$^9$ are independently selected from hydrogen, alkyl, hydroxyalkyl, alkoxyalkyl, cycloalkyl, substituted cycloalkyl, heterocyclyl, and substituted heterocyclyl;

R$^{10}$ is alkyl, cycloalkyl, substituted cycloalkyl, heterocyclyl, or substituted heterocyclyl; and p is 1 or 2.

More preferred are compounds of Formula (Ip), as immediately defined above, wherein R is

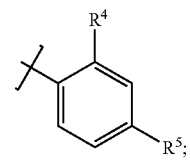

and R$^4$ and R$^5$ are both halogen.

According to one aspect of the invention, preferred compounds are compounds of Formula (Ip), as immediately defined above, wherein Q is selected from C$_{1-6}$alkyl or C$_{1-6}$alkyl substituted with one to two of hydroxy, —O(C$_{1-4}$ alkyl), —S(O)$_2$(C$_{1-4}$alkyl), C$_{3-7}$cycloalkyl, and/or a five to six membered monocyclic heterocyclic ring, wherein each of said rings is optionally-substituted with up to one of R$^{12}$ and/or up to one of R$^{14}$; and R$^{12}$ and R$^{14}$ are independently selected where valence allows from C$_{1-4}$alkyl, hydroxy, oxo (=O), —O(C$_{1-4}$alkyl), —C(=O)H, —C(=O)(C$_{1-4}$alkyl), —C(O)$_2$H, —C(O)$_2$(C$_{1-4}$alkyl), and —S(O)$_2$(C$_{1-4}$alkyl).

According to another aspect of the invention, preferred compounds are compounds of Formulae (I) and (Ip), wherein Q is an alkyl or substituted alkyl having the formula —C(R$^1$R$^2$R$^3$), wherein R$^1$, R$^2$ and R$^3$ are selected from hydrogen, alkyl, hydroxyalkyl, alkoxyalkyl, —(C$_{1-4}$-alkylene)—S(O)$_p$R$^{10}$, and —(C$_{1-4}$alkylene)—C(O)$_2$R$^8$ (wherein R$^8$ and R$^{10}$ are lower alkyl).

According to another aspect of the invention, preferred compounds are compounds of Formulae (I) and (Ip), where Q is an optionally-substituted C$_{3-7}$cycloalkyl, C$_{3-7}$cycloalkylalkyl, heterocyclyl, or heterocyclylalkyl. More preferred are compounds where Q is a C$_{1-4}$alkyl substituted with an optionally-substituted cyclohexyl, piperidin-4-yl, or tetrahydropyran-4-yl. Preferably, said cycloalkyl and heterocyclic groups are unsubstituted or in turn, are substituted with OH, —O(C$_{1-4}$alkyl), —C(O)$_2$(C$_{1-4}$alkyl) and/or —S(O)$_2$(C$_{1-4}$alkyl), more preferably with one of —C(O)$_2$ (Et) or —S(O)$_2$(CH$_3$).

In compounds of Formula (I) and (Ip), preferably R is di-substituted phenyl, more preferably 2,4-disubstituted phenyl, and even more preferably 2,4-dihalosubstituted phenyl. Most preferred are compounds where R is 2,4-difluorophenyl.

Another group of preferred compounds are those having the formula,

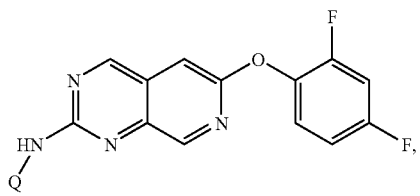

wherein Q is alkyl, cycloalkyl, substituted cycloalkyl, heterocyclyl, substituted heterocyclyl, or $C_{1-6}$alkyl substituted with one, two or three of halogen, cyano, haloalkoxy, —OR$^8$, —SR$^8$, —S(O)$_p$R$^{10}$, —C(O)$_2$R$^8$, cycloalkyl, substituted cycloalkyl, heterocyclyl and/or substituted heterocyclyl, wherein R$^8$ is selected from hydrogen, alkyl, and optionally-substituted cycloalkyl or heterocyclyl, and R$^{10}$ is alkyl or optionally-substituted cycloalkyl or heterocyclyl.

Another group of preferred compounds are those having the formula:

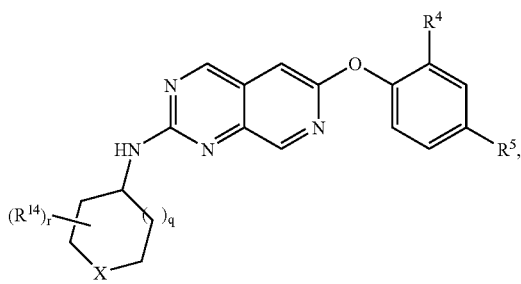

wherein:
R$^4$ and R$^5$ are both halogen (more preferably fluoro);
X is —O—, —C(=O)—, —N(R$^{12a}$)—, or —CH(R$^{12b}$)—;
R$^{12a}$ is selected from hydrogen, $C_{1-4}$ alkyl, —C(=O)R$^{15}$, —C(O)$_2$R$^{15}$, and —S(O)$_2$(C$_{1-4}$alkyl);
R$^{12b}$ is selected from hydrogen, $C_{1-4}$alkyl, —OR$^{15}$, —C(=O)R$^{15}$, —C(O)$_2$R$^{15}$, and —S(O)$_2$(C$_{1-4}$alkyl);
R$^{14}$ is selected from $C_{1-4}$alkyl, oxo(=O), —OR$^{15}$, —C(=O)R$^{15}$, —C(O)$_2$R$^{15}$, and —S(O)$_2$(C$_{1-4}$alkyl);
R$^{15}$ is at each occurrence selected from hydrogen and $C_{1-4}$alkyl;
q is 0 or 1; and
r is 0, 1 or 2.

Even more preferred are compounds as immediately defined above, wherein X is —NR$^{12a}$—, R$^{12a}$ is S(O)$_2$(C$_{1-4}$ alkyl), and q is 1.

UTILITY

Compounds of Formula I are useful for the treatment of any disorder or disease state in a human, or other mammal, which is exacerbated or caused by excessive or unregulated proinflammatory cytokines (i.e., TNF, IL-1, etc.), or p38 kinase activation by such mammal. Compounds of Formula I inhibit p38 kinase in in vitro assays and inhibit TNF-α or IL-1β release in cell based assays.

In view of their activity as inhibitors of p38 kinase, the compounds of the invention are useful for treating inflammatory diseases, autoimmune diseases, destructive bone disorders, proliferative disorders, angiogenic disorders, infectious diseases, neurodegenerative diseases, and viral diseases. Compounds of the invention are useful in treating arthritis, including but not limited to rheumatoid arthritis, spondylitis, gouty arthritis, osteoarthritis, systemic lupus erythematosus (SLE), juvenile arthritis, and other arthritic conditions. In addition, compounds of the present invention are useful in treating pulmonary disorders or lung inflammation, including adult respiratory distress syndrome, pulmonary sarcoidosis, asthma, silicosis, and chronic obstructive pulmonary disease. Furthermore, compounds of the present invention are useful in treating viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. Moreover, compounds of the present invention are useful in the treatment of bone resorption diseases, such as osteoporosis, endotoxic shock, toxic shock syndrome, reperfusion injury, autoimmune disease including graft vs. host reaction and allograft rejections, cardiovascular diseases including myocardial infarction, atherosclerosis, thrombosis, congestive heart failure, cardiac reperfusion injury, renal reperfusion injury, liver disease and nephritis, and myalgias due to infection.

The compounds of the present invention are also useful for the treatment of influenza, diabetes, skin-related conditions such as psoriasis, eczema, burns, dermatitis, keloid formation, and scar tissue formation. Compounds of the present invention are also useful in treating gastrointestinal conditions such as inflammatory bowel disease, Crohnxs disease, gastritis, irritable bowel syndrome, and ulcerative colitis. The compounds of the present invention can also be used in treating ophthalmic diseases, such as retinitis, retinopathies, uveitis, ocular photophobia, and acute injury to the eye tissue. Compounds of the invention also would be useful for treatment of cancer and angiogenesis, including neoplasia and metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant conditions such as hemangiomas, including infantile hemangiomas, angiofibroma of the nasopharynx and avascular necrosis of bone; diabetic nephropathy and cardiomyopathy; and disorders of the female reproductive system such as endometriosis.

The compounds of the present invention are also useful in treating central nervous system disorders, such as Alzheimer's disease, multiple sclerosis, and depression.

In addition, compounds of the present invention are also useful for preventing the production of cyclooxygenase-2 and thus are useful in treating those diseases responsive to inhibition of COX-2, such as fever, edema, and pain, including headache, neuromuscular pain, dental pain, arthritic pain and pain caused by cancer.

Besides being useful for human treatment, compounds of the present invention are also useful for veterinary treatment of animals such as companion, exotic, and farm animals, including mammals, rodents, and the like. More preferred animals include horses, dogs, and cats.

Furthermore, compounds of the present invention can be used in co-therapies, partially or completely, in place of other conventional anti-inflammatory agents, such as together with steroids, cyclooxygenase-2 inhibitors, NSAIDs, aspirin, DMARDS, immunosuppressive agents, 5-lipoxygenase inhibitors, LTB$_4$ antagonists and LTA$_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention. When reference herein is made generally to "TNF" inhibition, this is intended to encompass both TNF-α and TNF-β inhibition, unless specifically delineated otherwise.

ABBREVIATIONS

For ease of reference, the following abbreviations are used in the general synthetic schemes and Examples below:
EtOH=ethanol
MeOH=methanol
EtOAc=ethyl acetate
DCE=1,2-dichloroethane
DCM=dichloromethane
DMF=dimethylformamide
NaOH=sodium hydroxide
NMP=1-methyl-2-pyrrolidinone
Pd/C=palladium on carbon
TEA or Et$_3$N=triethylamine
TFA=trifluoroacetic acid
THF=tetrahydrofuran
TLC=thin layer chromatography
Mp=melting point
MW=molecular weight
h=hour(s)
rt.=room temperature

GENERAL SYNTHETIC SCHEMES

The compounds of the present invention can be prepared in a number of ways known to one skilled in the art. Preferred methods include, but are not limited to, the general synthetic procedures described below.

The starting materials and reagents used are either available from commercial suppliers such as Aldrich Chemical Co. (Milwaukee, Wis., USA), Bachem (Torrance, Calif., USA), Enika Chemie or Sigma (St. Louis, Mo., USA), Maybridge (Dist: Ryan Scientific, P.O. Box 6496, Columbia, S.C. 92960), etc.; or they can be prepared by methods known to those skilled in the art following procedures set forth in the literature. These schemes are merely illustrative; various modifications to these schemes can be made and will be apparent to one skilled in the art.

The starting materials and the intermediates of the reaction may be isolated and purified if desired using conventional techniques, including but not limited to filtration, distillation, crystallization, chromatography, and the like.

Such materials may be characterized using conventional means, including physical constants and spectral data. In the Schemes, the variables Q, R, R$^6$, R$^7$ etc., are defined as set forth in the Summary of Invention and claims.

General Scheme 1:

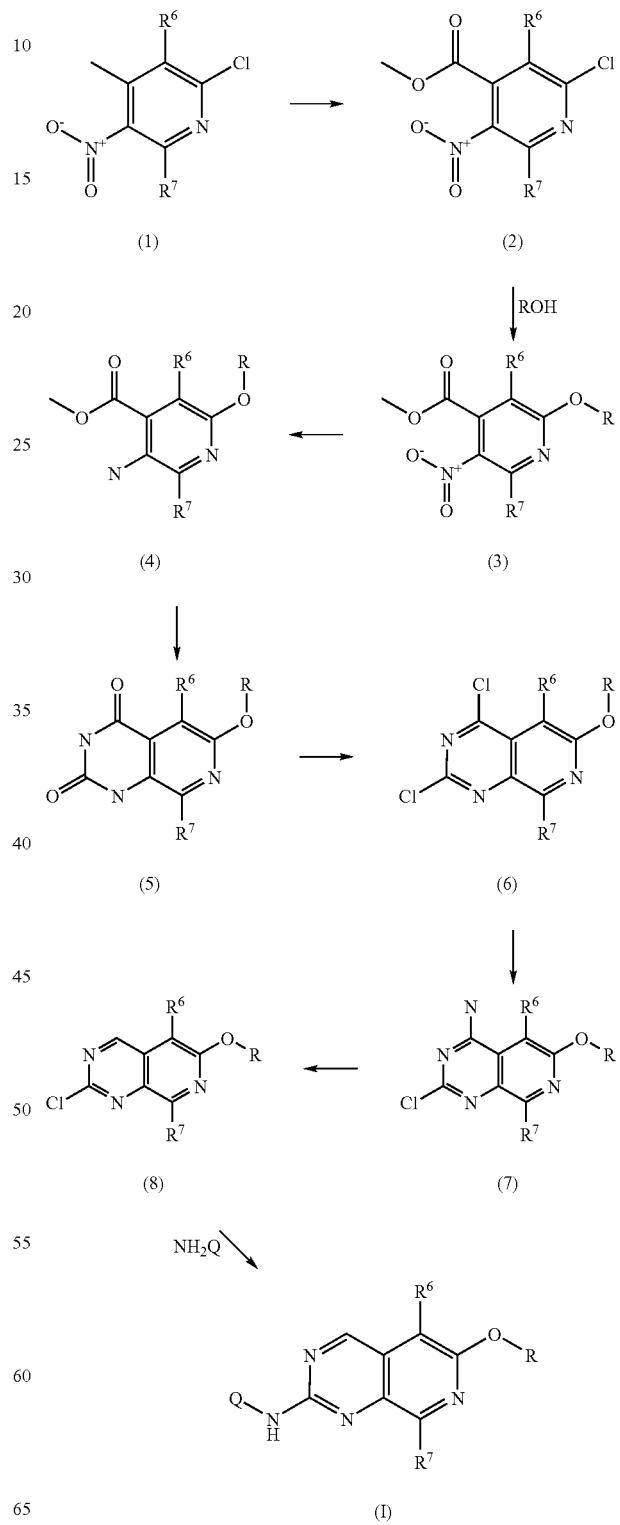

Compound (2) can be prepared from 2-chloro-4-methyl-5-nitropyridine (1) by treatment with an oxidant such as sodium dichromate dihydrate in concentrated sulfuric acid, followed by esterification with an appropriate agent such as trimethylsilyldiazo methane. Compound (2) can be converted to the desired 2-alkoxy or aryloxy 5-nitro-isonicotinic acid methyl ester (3) by treatment with an appropriate alcohol ROH and base such as sodium hydride. Treatment of compound (3) with hydrogen gas provides compound (4), which when reacted with urea provides pyridopyrimidine-2,4-dione (5). Compound (5) can be reacted with phosphorus oxychloride and N,N-diethyl aniline to provide dichloro compound (6), which upon treatment with ammonia in an appropriate solvent such as MeOH provides compound (7), which in turn can be converted to compound (8) upon treatment with tert-butylnitrite in solvent such as THF. Coupling of compound (8) with an appropriately-substituted amine $NH_2$-Q in solvent such as NMP provides compounds of formula (I).

Generic Scheme 2: Preparation of N-oxides

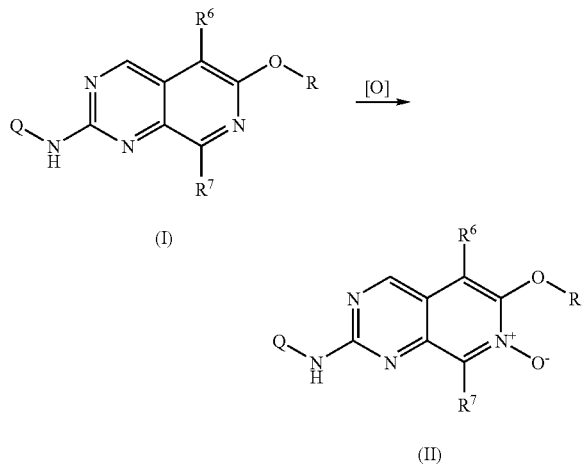

Compounds of general formula (I) can be converted to the corresponding N-oxides of formula (II) by treatment with an appropriate oxidizing agent such as dimethyl dioxirane, urea peroxide, or methyltrioxorhenium/$H_2O_2$.

EXAMPLE 1

[6-(2,4-Difluoro-phenoxy)-pyrido[3,4-d]pyrimidin-2-yl]-(1-methanesulfonyl-piperidin-4-yl)-amine

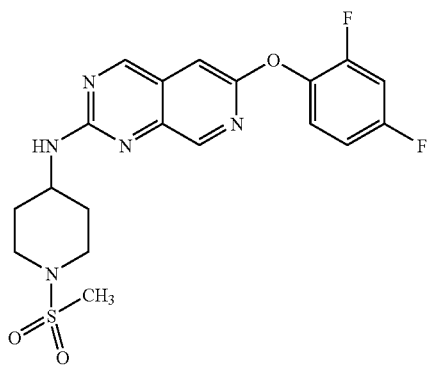

1A. 2-Chloro-5-nitro-isonicotinic acid methyl ester

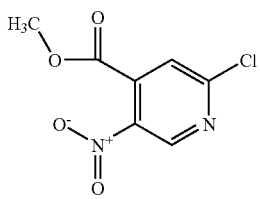

To a solution of 2-chloro-4-methyl-5-nitropyridine (Aldrich Chemical Co.) (5.0 g, 29.0 mmol) in concentrated sulfuric acid (60 mL) with stirring at 0° C., was added a solution of sodium dichromate dihydrate (14.3 g, 1.65 eq) in concentrated sulfuric acid (100 mL) at a rate which kept the internal temperature less than 10° C. After addition was complete, the reaction mixture was stirred from 0° C. to room temperature over 6 hours. By TLC, the reaction was not complete, so additional sodium dichromate dihydrate (8.4 g, 1 eq) was added directly to the solution at 0° C. The resulting solution was stirred from 0° C. to room temperature overnight. The reaction was complete by TLC the next morning, and it was poured into a mixture of ice (1 L) and EtOAc (900 mL). The resulting mixture was stirred for about 10 minutes and then the layers were separated. The organic layer was washed with brine (2×600 mL), and the EtOAc layer was dried over magnesium sulfate and filtered. With stirring at room temperature, trimethylsilyl diazomethathane (2.0M in hexanes, 15 mL) was added to the EtOAc filtrate. The resulting mixture was stirred at room temperature for 30 min. By TLC, there was no acid remaining, and then MeOH (150 mL) was added and the solution stirred for 30 minutes. The solution was concentrated and then EtOAc (700 mL) was added to the residue which was dried over magnesium sulfate, filtered, concentrated and pumped to give the title compound (1A) as an off-white powder (5.79 g, $M^+$=216, M.P.=60.5–64.1° C.).

1B. 2-(2,4-Difluoro-phenoxy)-5-nitro-isonicotinic acid methyl ester

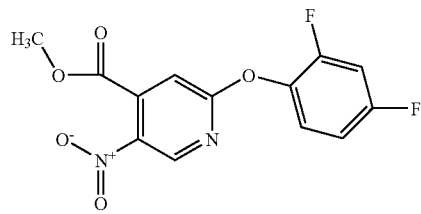

To 2,4 difluorophenol (Aldrich Chemical Co.) (2.68 mL, 1.1 eq) in THF (60 mL) at 0° C. was added sodium hydride (60% in oil) (1.123 g, 1.1 eq), and the resulting mixture was stirred from 0° C. to room temperature over 1 hour. This solution was then added to compound (1A) (5.79 g, 26.7 mmol), and the resulting mixture was heated at reflux for 2 hours. TLC analysis confirmed that the reaction was complete, and the mixture was cooled to room temperature. EtOAc (300 mL) and water (100 mL) were added, the resulting mixture was partitioned, and the layers were separated. The organic layer was washed with water (3×100 mL) and brine (1×100 mL). Then the EtOAc layer was dried over magnesium sulfate, filtered, concentrated, and pumped to give the titled compound (1B) as an off-white powder (7.99 g, M+=310, Mp=90.2–91.4° C.)

1C. 5-Amino-2-(2,4-difluoro-phenoxy)-isonicotinic acid methyl ester

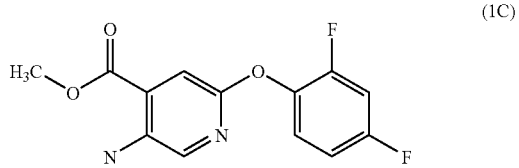

Compound (1B) (7.99 g, 25.6 mmol) was taken up in EtOH (350 mL), and nitrogen gas was bubbled through the solution for five minutes before 10% Pd/C (1.6 g) was carefully added. The resulting mixture was put on the Parr Shaker under 60 psi hydrogen gas for 4 hours. By TLC, there was no starting material remaining. The reaction mixture was filtered through a 3 cm bed of celite, and the filtrate was concentrated to give 7.0 g of crude product. Purification by column chromatography eluting on 130 g of silica gel with a gradient of 5% EtOAc in hexanes through 10% EtOAc in hexanes afforded the titled compound (1C) as an off-white powder (4.223 g, (M+H)+=281, Mp=102.0–103.9° C.).

1D. 6-(2,4-Difluoro-phenoxy)-1H-pyrido[3,4-d]pyrimidine-2,4-dione

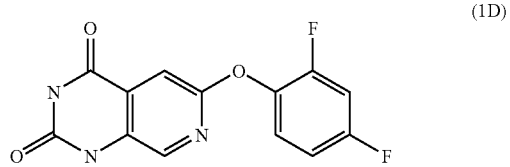

Compound (1C) (4.2 g, 15.0 mmol) and urea (9.0 g, 10 eq) were heated to a melt at 160° C. with stirring. After 2 hours, the melt solidified and by TLC the reaction was complete. The reaction mixture was cooled to room temperature, water (250 mL) was added, and the resulting mixture was left to stand for 1 hour. Then the solids were broken up with a spatula and the mixture was stirred vigorously for 1 hour. After suction filtration, a tan powder was collected which was air-dried in the frit for two days. Drying under high vacuum at 56° C. gave the title compound (1D) as a tan powder (4.307 g, (M−H)−=290, M.P.>300° C.).

1E. 2,4-Dichloro-6-(2,4-difluoro-phenoxy)-pyrido[3,4-d]pyrimidine

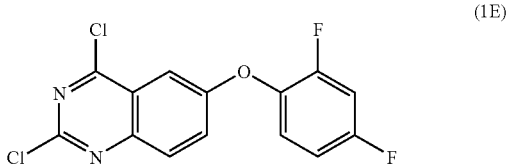

Compound (1D) (4.2 g, 14.4 mmol) was taken up in phosphorus oxychloride (55 mL), and then N,N-diethyl aniline (1.34 mL, 0.6 eq) was added. The resulting mixture was heated to reflux with stirring for 2 hours. TLC analysis confirmed that the reaction was complete. The reaction mixture was concentrated under reduced pressure at 55° C. and then EtOAc (600 mL) was added to the residue. At 0° C., sodium carbonate$_{(aq)}$ (pH=12) solution (300 mL) was slowly added, and then the resulting mixture was stirred for 20 minutes. The layers were separated, then another 300 mL of sodium carbonate$_{(aq)}$ (pH=12) solution was added, and the resulting mixture was stirred for 15 minutes. The combined aqueous layers were extracted with EtOAc (1×200 mL), and the combined organic layers were finally washed with brine (1×300 mL). The organic layer was dried over magnesium sulfate, filtered and concentrated. The crude product was purified by column chromatography eluting on 130 g of silica gel with 3% EtOAc in hexanes to give the title compound (1E) as an off-white powder (3.584 g, M+=327, Mp =144.3–146.2° C.)

1F. 2-Chloro-6-(2,4-difluoro-phenoxy)-pyrido[3,4-d]pyrimidine-4-ylamine

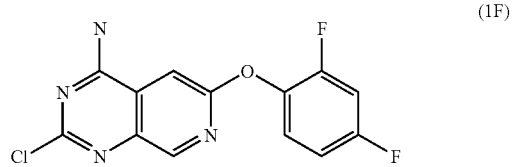

Compound (1E) (1.75 g, 5.33 mmol) was placed in a sealed-tube, and 7 N ammonia in MeOH (Aldrich Chemical Co.) (30 mL) was added. The tube was tightly capped, and the resulting homogeneous mixture was stirred at room temperature overnight. The next morning, TLC confirmed that the reaction was complete. The mixture was transferred to a round-bottom flask and concentrated under reduced pressure at 55° C. The residue was taken up in EtOAc (700 mL) and water (250 mL). The layers were partitioned and then separated. The organic layer was washed with water (2×250 mL) and brine (1×250 mL). The organic layer was dried over magnesium sulfate, filtered, concentrated, and pumped to give the title compound (1F) as an off-white powder (1.859 g, (M−H)−=307, Mp>300° C.).

1G. 2-Chloro-6-(2,4-difluoro-phenoxy)-pyrido[3,4-d]pyrimidine

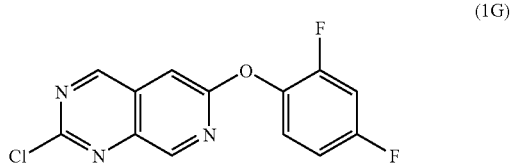

Compound (1F) (1.8 g, 5.83 mmol) was taken up in THF (100 mL) and tert-butylnitrite (Aldrich Chemical Co.) was added. The resulting mixture was heated to reflux with stirring for 48 hours and additional tert-butyl nitrite was added in portions (total 5 mL). By TLC, the reaction was complete. After cooling to room temperature, the solvent was removed under reduced pressure at 55° C. EtOAc (180 mL) and water (60 mL) were added to the residue, and the layers were partitioned and separated. The organic layer was washed with water (3×60 mL) and brine (1×60 mL). After drying over magnesium sulfate, the organic layer was filtered, concentrated and pumped to give a crude oil (3.14 g). Purification by column chromatography eluting on 68 g of silica gel with 5% EtOAc in hexanes afforded the title compound (1G) as a yellow powder (0.546 g, M⁺=293).

1H. [6-(2,4-Difluoro-phenoxy)-pyrido[3,4-d]pyrimidin-2-yl-(1-methanesulfonyl-piperidin-4-yl)-amine (Example 1)

Compound (1G) (200 mg, 0.68 mmol) and 1-methanesulfonyl-piperidin-4-ylamine (365 mg, 3 eq) in NMP were heated at 90° C. with stirring for 1 hour. By TLC, the reaction was complete and allowed to cool to room temperature. EtOAc (80 mL) and water (40 mL) were added, and the layers were partitioned and separated. The organic layer was washed with water (3×40 mL) and brine (1×40 mL). The EtOAc layer was then dried over magnesium sulfate, filtered, and concentrated. Purification by preparative TLC eluting with 5% MeOH in DCM afforded the above-titled compound (Example 1) as a yellow powder (0.185 g, (M+H)⁺=436, Mp=209.9–211.9° C.).

EXAMPLES 2–5

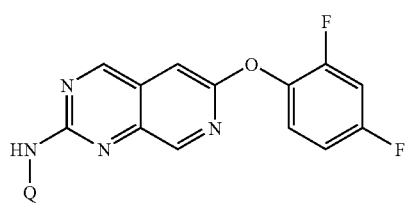

(Ib)

Compounds having the Formula (Ib) above, wherein Q has the values set forth in Table 1, were prepared following the same or similar method as described above for Example 1, except the appropriately-substituted amine was used in place of 1-(methylsulfonyl) piperidin-4-yl amine in step 1H.

TABLE 1

| Ex. No. | Q | Compound Name | MW |
|---|---|---|---|
| 2 | (isopropyl) | [6-(2,4-Difluoro-phenoxy)-pyrido[3,4-d]pyrimidin-2-yl]-iso-propyl-amine | 316.31 |
| 3 | (pentane-1,5-diol chain) | 3-[6-(2,4-Difluoro-phenoxy)-pyrido[3,4-d]pyrimidin-2-ylamino]-pentane-1,5-diol | 376.36 |
| 4 | (tetrahydropyran-4-yl) | [6-(2,4-Difluoro-phenoxy)-pyrido[3,4-d]pyrimidin-2-yl]-(tetrahydro-pyran-4-yl)-amine | 358.34 |
| 5 | (4-hydroxycyclohexyl) | 4-[6-(2,4-Difluoro-phenoxy)-pyrido[3,4-d]pyrimidin-2-ylamino]-cyclohexanol | 372.37 |

EXAMPLE 6

The following are representative pharmaceutical formulations containing a compound of Formula (I) or (II).

Tablet Formulation

The following ingredients are mixed intimately and pressed into single scored tablets.

| Ingredient tablet, mg | Quantity per |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient capsule, mg | Quantity per |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| Sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
|---|---|
| compound of the invention | 500 mg |
| Witepsol ® H-15 | balance |

EXAMPLE 7

Inhibition of p38 (MAP) Kinase-In Vitro Assay

The p-38 MAP kinase inhibitory activity of compounds of this invention in vitro was determined by measuring the transfer of the y-phosphate from $\gamma\text{-}^{33}\text{P-ATP}$ by p38 kinase to Myelin Basic Protein (MBP), using the a minor modification of the method described in Ahn et al., *J. Biol. Chem.*, Vol. 266 (7), 4220–4227 (1991).

The phosphorylated form of the recombinant p38 MAP kinase was expressed with SEK-1 and MEKK in *E. Coli* (see Khokhlatchev et al., *J. Biol. Chem.* Vol. 272(17), pp. 11057–11062 (1997)), and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added, and the samples were incubated for 10 min. at 30° C. The kinase reaction was initiated by the addition of a substrate cocktail containing MBP and $\gamma\text{-}^{33}\text{P-ATP}$. After incubating for an additional 20 min. at 30° C., the reaction was terminated by adding 0.75% phosphoric acid. The phosphorylated MBP was then separated from the residual $\gamma\text{-}^{33}\text{P-ATP}$ using a phosphocellulose membrane (Millipore, Bedfrod, Mass.) and quantitated using a scintillation counter (Packard, Meriden, Conn.).

EXAMPLE 8

This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation*, 51:498–503 (1991).

(a) Induction of TNF Biosynthesis:

THP-1 cells were suspended in culture medium [RPMI (Gibco-BRL, Gailthersburg, Md.) containing 10% fetal bovine serum, 0.02 mM 2-mercaptoethanol], at a concentration of $2.5 \times 10^6$ cells/mL and then plated in 96 well plate (0.2 mL aliquots in each well). Test compounds were dissolved in DMSO and then diluted with the culture medium such that the final DMSO concentration was 5%. Twenty five µL aliquots of test solution or only medium with DMSO (control) were added to each well. The cells were incubated for 30 min., at 37° C. LPS (Sigma, St. Louis, Mo.) was added to the wells at a final concentration of 0.5 µg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. *GUT.* Vol. 39(5), 684–689 (1996).

Polystyrene 96-well plates were coated with 50 µl per well of antibody 2TNF-H12 in PBS (5 µg/mL) and incubated in a humidified chamber at 4° C. overnight. The plates were washed with PBS and then blocked with 3% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five µL aliquots of the above culture supernatants or TNF standards or only medium (control) were mixed with 25 µL aliquots of biotinylated monoclonal antibody 2TNF-H34 (1 µg/mL in PBS containing 0.1% BSA) and then added to each well. The samples were incubated for 2 hr at room temperature with gentle shaking and then washed 3 times with 0.1% BSA in PBS. 50 µL of peroxidase-streptavidin (Zymed, S. San Francisco, Calif.) solution containing 0.416 µg/mL of peroxidase-streptavidin and 0.1% BSA in PBS was added to each well. The samples were incubated for an additional 1 hr at room temperature and then washed 3 times with 0.1% BSA in PBS. Fifty µL of O-phenylenediamine solution (1 µg/mL O-phenylenediamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The $IC_{50}$ value was defined as the concentration of the test compound corresponding to half-maximal reduction in 450 nm absorbance.

The compounds described in the Examples herein were tested in the above assay and found to have a measurable level of p38 inhibitory activity. As an illustration, Table 2 below lists approximate p38 inhibitory activities that were detected for certain compounds according to the invention (expressed as $IC_{50}$, the concentration causing 50% inhibition of the p38 enzyme being analyzed).

TABLE 2

| Ex. No. | $IC_{50}$ µM (P38 MAP KINASE E-03) |
|---|---|
| 1 | <.05 |
| 2 | <.5 |
| 4 | <.3 |

The foregoing discussion of the invention has been presented for purposes of illustration and description. The foregoing is not intended to limit the invention to the forms disclosed herein. Although the description of the invention has included one or more embodiments and certain variations and modifications, other variations and modifications are within the scope of the invention, e.g., as may be within the skill and knowledge of those in the art. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety.

The invention claimed is:

1. A compound having the Formula (I) or (II):

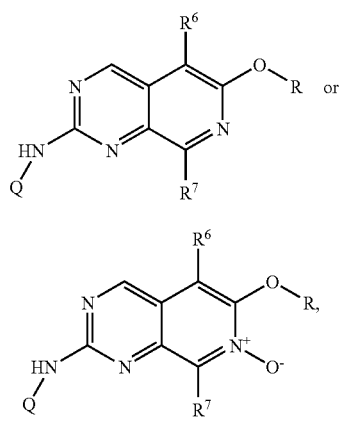

or a pharmaceutically-acceptable salt thereof, wherein:
R is selected from:
(a) alkyl optionally-substituted with one to three of $R^{17}$;
(b) cycloalkyl optionally substituted with one, two or three groups selected from $R^{18}$; and
(c) optionally-substituted aryl;
Q is selected from alkyl, cycloalkyl, substituted cycloalkyl, heterocyclyl, substituted heterocyclyl, and alkyl substituted with one, two or three of halogen, cyano, —$OR^8$, —$SR^8$, —C(=O)$R^8$, —C(O)$_2R^8$, —C(=O)$NR^8R^9$, —S(O)$_pR^{10}$, —C(O)$_2NR^8R^9$, —S(O)$_2NR^8R^9$, —$NR^8R^9$, cycloalkyl, substituted cycloalkyl, heterocyclyl, and/or substituted heterocyclyl;
$R^6$ is hydrogen or lower alkyl;
$R^7$ is selected from hydrogen, alkyl, substituted alkyl, halogen, cyano, nitro, hydroxy, alkoxy, haloalkoxy, amino, alkylamino, and optionally-substituted cycloalkyl, heterocyclyl, aryl, or heteroaryl;
$R^8$ and $R^9$ are (i) independently selected from hydrogen, alkyl, haloalkyl, hydroxyalkyl, alkoxyalkyl, cycloalkyl, substituted cycloalkyl, heterocyclyl, and substituted heterocyclyl; or (ii) when $R^8$ and $R^9$ are attached to the same nitrogen atom (as in —C(O)$_2NR^8R^9$, —S(O)$_2NR^8R^9$, and —$NR^8R^9$), $R^8$ and $R^9$ may be taken together to form an optionally-substituted heterocyclyl ring;
$R^{10}$ is alkyl, hydroxyalkyl, alkoxyalkyl, cycloalkyl, substituted cycloalkyl, heterocyclyl, or substituted heterocyclyl;
$R^{17}$ is at each occurrence independently selected from halogen, haloalkoxy, haloalkyl, alkoxy, or optionally-substituted phenyl, benzyl, phenyloxy, benzyloxy, or cycloalkyl;

$R^{18}$ is at each occurrence independently selected from alkyl, substituted alkyl, halogen, haloalkyl, haloalkoxy, cyano, alkoxy, acyl, alkoxycarbonyl, alkylsulfonyl, or optionally-substituted phenyl, phenyloxy, benzyloxy, cycloalkyl, heterocyclyl, or heteroaryl; and p is 1 or 2.

2. A compound according to claim 1, or a pharmaceutically-acceptable salt thereof, wherein:
Q is selected from an alkyl or substituted alkyl having the formula —C($R^1R^2R^3$);
$R^1$, $R^2$ and $R^3$ are selected from hydrogen, alkyl, hydroxyalkyl, alkoxyalkyl, —(C$_{1-4}$alkylene)—S(O)$_pR^{10}$, —(C$_{3-4}$alkylene)—C(O)$_2R^8$, cycloalkyl, cycloalkylalkyl, heterocyclyl, or heterocycloalkyl, wherein said cycloalkyl and heterocyclyl groups are, in turn, optionally substituted with up to one of $R^{12}$ and up to one of $R^{14}$; and
$R^{12}$ and $R^{14}$ are independently selected where valence allows from C$_{1-4}$alkyl, hydroxy, oxo (=O), —O(C$_{1-4}$alkyl), —C(=O)H, —C(=O)(C$_{1-4}$alkyl), —C(O)$_2$H, —C(O)$_2$(C$_{1-4}$alkyl), and —S(O)$_2$(C$_{1-4}$alkyl).

3. A compound according to claim 1, or a pharmaceutically-acceptable salt thereof, wherein R is phenyl substituted with one to two of lower alkyl, halogen, haloalkyl, haloalkoxy, cyano, and nitro.

4. A compound according to claim 1, or a pharmaceutically-acceptable salt thereof, wherein R is:

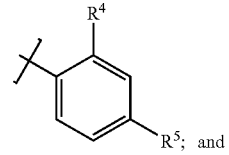; and $R^4$ and $R^5$ are selected from halogen, haloalkyl, haloalkoxy, and cyano.

5. A compound according to claim 4, or a pharmaceutically-acceptable salt thereof, wherein:
$R^4$ and $R^5$ are both halogen.

6. A compound according to claim 1, or a pharmaceutically-acceptable salt thereof, wherein $R^6$ and $R^7$ are both hydrogen.

7. A compound according to claim 1, or a pharmaceutically-acceptable salt thereof, wherein Q is C$_{1-6}$alkyl or hydroxy(C$_{1-6}$alkyl).

8. A compound according to claim 1, or a pharmaceutically-acceptable salt thereof, wherein Q is an optionally-substituted C$_{3-7}$cycloalkyl or an optionally-substituted heterocyclic ring.

9. A compound according to claim 1, or a pharmaceutically-acceptable salt thereof, wherein:
Q is cyclohexyl, piperidin-4-yl, or tetrahydropyran-4-yl, wherein each of said rings in turn is optionally-substituted with up to two of lower alkyl, —OH, —C(O)$_2$(C$_{1-4}$alkyl) and/or —S(O)$_2$(CH$_3$).

10. A compound according to claim 1, or a pharmaceutically-acceptable salt thereof, having the formula:

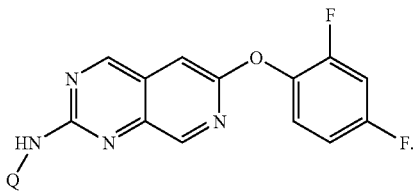

11. A compound according to claim 1, or a pharmaceutically-acceptable salt thereof, having the formula:

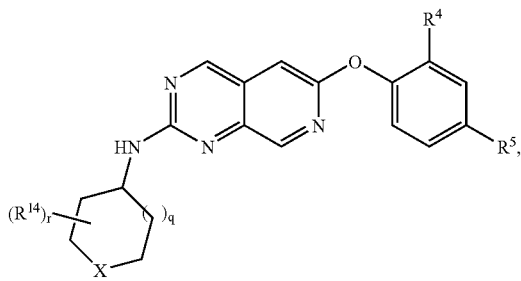

wherein:

X is —O—, —C(=O)—, —N($R^{12a}$)—, or —CH($R^{12b}$)—;

$R^{12a}$ is selected from hydrogen, $C_{1-4}$alkyl, —C(=O)$R^{15}$, —C(O)$_2R^{15}$, and —S(O)$_2$($C_{1-4}$alkyl);

$R^{12b}$ is selected from hydrogen, $C_{1-4}$alkyl, —O$R^{15}$, —C(=O)$R^{15}$, —C(O)$_2R^{15}$, and —S(O)$_2$($C_{1-4}$alkyl);

$R^{14}$ is selected from $C_{1-4}$alkyl, oxo (=O), —O$R^{15}$, —C(=O)$R^{15}$, —C(O)$_2R^{15}$, and —S(O)$_2$($C_{1-4}$alkyl);

$R^{15}$ is selected from hydrogen and $C_{1-4}$alkyl;

q is 0 or 1; and r is 0, 1 or 2.

12. A compound according to claim 11, or a pharmaceutically-acceptable salt thereof, wherein:

$R^4$ and $R^5$ are both fluoro.

13. A compound according to claim 11, or a pharmaceutically-acceptable salt thereof, wherein X is —N$R^{12a}$—, $R^{12a}$ is —S(O)$_2$($C_{1-4}$alkyl), and q is 1.

14. A compound having the Formula (Ip),

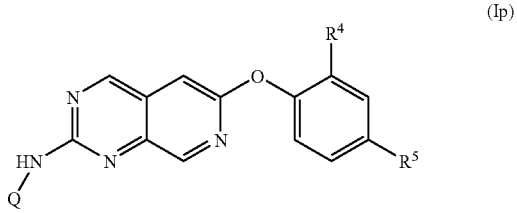

or a pharmaceutically-acceptable salt thereof, wherein:

Q is alkyl, substituted alkyl or an optionally-substituted cycloalkyl or heterocyclyl, provided Q is not arylalkyl or heteroarylalkyl; and $R^4$ and $R^5$ are both halogen.

15. A compound according to claim 14, or a pharmaceutically-acceptable salt thereof, wherein $R^4$ and $R^5$ are both fluoro.

16. A compound according to claim 14, or a pharmaceutically-acceptable salt thereof, wherein Q is an optionally-substituted monocyclic cycloalkyl or heterocyclyl ring.

17. A pharmaceutical composition comprising a therapeutically effective amount of compound according to claim 1, or a pharmaceutically-acceptable salt thereof, in combination with a pharmaceutically-acceptable excipient.

18. A process for preparing a compound of formula (I)

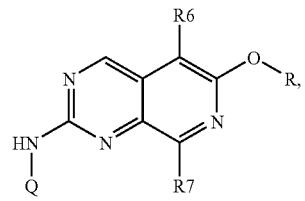

wherein R is selected from:

(a) alkyl optionally-substituted with one to three of $R^{17}$;

(b) cycloalkyl optionally substituted with one, two or three groups selected from $R^{18}$; and (c) optionally-substituted aryl;

Q is selected from alkyl, cycloalkyl, substituted cycloalkyl, heterocyclyl, substituted heterocyclyl, and alkyl substituted with one, two or three of halogen, cyano, —O$R^8$, —S$R^8$, —C(=O)$R^8$, —C(O)$_2R^8$, —C(=O)N$R^8R^9$, —S(O)$_pR^{10}$, —C(O)$_2$N$R^8R^9$, —S(O)$_2$N$R^8R^9$, —N$R^8R^9$, cycloalkyl, substituted cycloalkyl, heterocyclyl, and/or substituted heterocyclyl;

$R^6$ is hydrogen or lower alkyl;

$R^7$ is selected from hydrogen, alkyl, substituted alkyl, halogen, cyano, nitro, hydroxy, alkoxy, haloalkoxy, amino, alkylamino, and optionally-substituted cycloalkyl, heterocyclyl, aryl, or heteroaryl;

$R^8$ and $R^9$ are (i) independently selected from hydrogen, alkyl, haloalkyl, hydroxyalkyl, alkoxyalkyl, cycloalkyl, substituted cycloalkyl, heterocyclyl, and substituted heterocyclyl; or (ii) when $R^8$ and $R^9$ are attached to the same nitrogen atom, $R^8$ and $R^9$ may be taken together to form an optionally-substituted heterocyclyl ring;

$R^{10}$ is alkyl, hydroxyalkyl, alkoxyalkyl, cycloalkyl, substituted cycloalkyl, heterocyclyl, or substituted heterocyclyl;

$R^{17}$ is at each occurrence independently selected from halogen, haloalkoxy, haloalkyl, alkoxy, or optionally-substituted phenyl, benzyl, phenyloxy, benzyloxy, or cycloalkyl;

$R^{18}$ is at each occurrence independently selected from alkyl, substituted alkyl, halogen, haloalkyl, haloalkoxy, cyano, alkoxy, acyl, alkoxycarbonyl, alkylsulfonyl, or optionally-substituted phenyl, phenyloxy, benzyloxy, cycloalkyl, heterocyclyl, or heteroaryl; and p is 1 or 2;

wherein said process comprises:
(i) providing a compound of formula (8); and
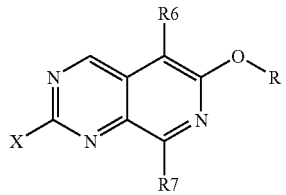
(5)
where X is a leaving group; and
(ii) contacting said compound of formula (8) with a compound of the formula NH₂Q in a polar, aprotic solvent.
19. The process of claim 18, wherein said compound of formula (8) is provided by treating a compound of formula (7) with t-butylnitrite:
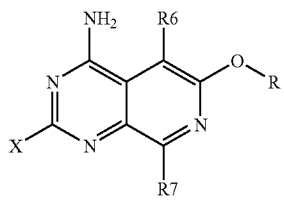
* * * * *